United States Patent [19]

Coutelle et al.

[11] Patent Number: 5,582,638
[45] Date of Patent: Dec. 10, 1996

[54] THICKENING AGENT BASED ON AT LEAST ONE SYNTHETIC PHYLLOSICATE

[75] Inventors: Helmut Coutelle, Freising; Wolfgang Heininger, Moosburg; Wolfgang Buckl, Horgertshausen, all of Germany

[73] Assignee: Sud-Chemie AG, Munich, Germany

[21] Appl. No.: 410,828

[22] Filed: Mar. 27, 1995

[30] Foreign Application Priority Data

Mar. 28, 1994 [DE] Germany .......................... 44 10 727.7

[51] Int. Cl.⁶ ................................ C08K 9/04; C09L 3/08
[52] U.S. Cl. ................................ 106/287.23; 106/287.17; 106/287.26
[58] Field of Search ...................... 106/282.17, 287.23, 106/287.26

[56] References Cited

U.S. PATENT DOCUMENTS

| | | |
|---|---|---|
| 4,382,868 | 5/1983 | House . |
| 4,412,018 | 10/1983 | Finlayson et al. . |
| 4,434,075 | 2/1984 | Mardis et al. . |
| 4,434,076 | 2/1984 | Mardis et al. ............. 106/287.17 |
| 4,517,112 | 5/1985 | Mardis et al. ............. 106/287.17 |
| 4,800,041 | 1/1989 | Tymon et al. . |
| 5,128,067 | 7/1992 | Placek . |
| 5,130,463 | 7/1992 | Haubennestal et al. . |
| 5,151,218 | 9/1992 | Haubennestal et al. . |
| 5,336,647 | 8/1994 | Noe et al. . |

FOREIGN PATENT DOCUMENTS

| | | |
|---|---|---|
| 3145457 | 9/1982 | Germany . |
| 3230476 | 2/1984 | Germany . |
| 3914916 | 11/1990 | Germany . |
| 899617 | 1/1982 | U.S.S.R. . |

OTHER PUBLICATIONS

Kittel, Hans: Lehrbuch der Lacke und Beschichtungen, Verlag W. A. Colomb in der H. Heenemann GbmH, Berlin–Oberschwandorf, (1974) Bd. II., 5,340,341.

Van Doren, Robert E., et al; The Role of Rheological Additives in Protective Coatings: Journal of Protective Coatings and Linings, (May 1989), pp. 47–52.

Primary Examiner—David Brunsman
Attorney, Agent, or Firm—Scott R. Cox

[57] ABSTRACT

A thickening agent which is based on at least one synthetic phyllosilicate which contains at least one additive from the group of organic phosphorus compounds comprising the following:

a) phosphonic acids with formula

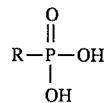

b) phosphinic acids with formula

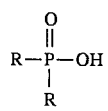

c) thiophosphinic acids with formula

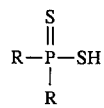

d) diesters of phosphorous acid with formula HO—P(OR)₂
e) diesters of phosphoric acid with formula

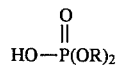

f) diphosphonic acid with formula

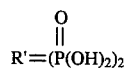

in which R is an alkyl or hydroxyalkyl group with 1 to 22 C atoms or an aryl or hydroxyaryl group with 6 to 12 C atoms and R' is an alkylene group with 2 to 22 C atoms.

14 Claims, No Drawings

THICKENING AGENT BASED ON AT LEAST ONE SYNTHETIC PHYLLOSICATE

BACKGROUND OF INVENTION

The invention relates to thickening agents based on at least one synthetic phyllosilicate.

In liquid or flowable coating systems, such as paints, varnishes, adhesives, printing inks, undersealing compositions, drilling fluids, cosmetic and pharmaceutical formulations, phyllosilicates are used to solve a number of problems such as settling of heavy pigments or active agents during storage, making available the necessary layer thickness for protective reasons, making available the viscosity suitable for the particular application, etc.

These phyllosilicates can form thixotropic "house-of-card" structures which impart the desired properties to the systems. Since these products themselves have a strong thickening action, which is certainly the reason for their use, the materials are not offered or marketed in predispersed form. This is due mainly to the fact that only pastes having a solids content of 2 to 8% can be produced and handled as a suspension. With the product essentially comprised of water, transportation of the product is not economically feasible.

Moreover, too much water can be brought into the formulation. This can result in the desired thickening effect of the phyllosilicate being neutralized by the high additional amount of water.

Moreover, a good dispersion of powders is a problem with phyllosilicates. Either the dispersion is not complete and the material is only partially used, (this also leads to other problems such as seeds (coarse particles) formation, post-thickening phenomena, loss of gloss and efficiency), or the dispersion is not possible in the desired formulation as the result of a lack of water and thus the possibility of compensating for the lacking mechanical dispersion forces by swelling with water. Even if the necessary mechanical dispersion energy is available, in many cases dispersion cannot be completely effected, as the components of the formulation are not always shear-stable. Uncontrollable post-thickening effects are thus the result and in some circumstances also seed formation, agglomerates and loss of gloss.

The addition of dispersion agents to improve dispersion is known in the art. However, this addition is normally done only after the phyllosilicate has been prewetted in water. The phyllosilicate is generally prewetted because most dispersion agents are highly polar and thus, can become attached to the edges of the phyllosilicate lamellae, such that hydration is suppressed and the opposite effect from dispersion is achieved. Dispersion agents, for example, based on acrylate or acrylamide, have a tendency to flocculate suspensions. This naturally reduces the viscosity of a phyllosilicate gel and also results in poor delamination and dispersion.

A process for producing organophilic clays with improved dispersibility in organic liquids is known from U.S. Pat. No. 4 382 868, in which a mixture of a smectite clay, a quaternary ammonium or phosphonium compound, water and an alcohol with 1 to 5 carbon atoms is extruded and the resulting organoclay gelatinization agent is ground without removing the water or alcohol. The product is no longer a clay which is capable of swelling in water.

A flame-inhibiting lubricant is known from U.S. Pat. No. 5,128,067 which contains a mixture of alkoxy and phenyl triesters of a phosphorus oxy acid and a fine-particle silica-containing thickening agent, for example, clay and silica. However, it is not a conversion product.

Organophilic clays are known from U.S. Pat. No. 5 336 647 which discloses the reaction product of a smectite clay with a first organic cation and a second organic cation from a polyalkoxylated quaternary ammonium salt. The clay is no longer present in hydrophilic form.

A gel-forming organophilic clay is known from DE-C-3 145 452 which discloses the reaction product of a clay of the smectite type with an organic anion (for example, a phosphite or phosphate) and an organic cation, for example, a quaternary ammonium or phosphonium compound. The conversion product is no longer hydrophilic.

An agent for enhancing the viscosity in nonaqueous liquid phases is known from DE-A-3 914 916 which is formed from finely dispersed particles of an inorganic laminar compound with positive layer charge based on two dimensional inorganic polycations (polycationic laminar compounds) and mono- and/or polybasic acid anions of a pronounced oleophilic nature. This product is not capable of swelling in water.

A gel-forming organophilic clay is disclosed in DE-A-3 145 475, which represents the reaction product of an organic cation, an organic anion and a clay of the smectite type. The organic cation is chosen from the group of quaternary ammonium salts, phosphonium salts and/or sulfonium salts. This product is not capable of swelling in water.

Use of phosphoric acid esters and their salts as dispersion agents and dispersion stabilizers for pigments in dyes, paints, and synthetic resins is known from DE-A-3 930 687. Aluminum hydroxide, zinc stearate, calcium carbonate, magnesium oxide and carbon black are named as pigments.

Easily dispersible organosmectites are known from DE-C-3 230 476 which contains exchangeable cations which have been replaced up to 50% by organic cations and which contains a surface which is covered with a peptising agent which is chosen from the group of sodium tetrapolyphosphate, sodium tripolyphosphate, sodium silicate, pyrogallol, gallic acid, and tannate. This product is also no longer capable of swelling in water.

It is known from Kittel, *Hans: Lehrbuch der Lacke und Beschichtungen* (Textbook of Paints and Coatings), Verlag W.A. Colomb in H. Heenemann GmbH, Berlin-Oberschwandorf, 1974, volume II, pp. 340, 341 that silicates, for example, minerals of the montmorillonite type, can be used as additives for paints. No information is disclosed on the modification of these substances for purposes of better dispersibility.

Rheological additives or thickening agents for pigment-containing protective coatings are known from Van Doren, Robert E., et al.: "The Role of Rheological Additives in Protective Coatings"; *Journal of Protective Coatings and Linings*, May 1989, pp. 47–52. Among those disclosed are pyrogenic silicic acids, cellulose-containing thickening agents, acrylates, and polyester-polyurethanes.

The objective of the invention is therefore to improve the dispersibility of phyllosilicates such that a powdered material can be easily dispersed at low to medium shearing forces without seeds. Another object is to provide pumpable pastes which can be easily metered and in which the phyllosilicate is present in completely dispersed form.

SUMMARY OF INVENTION

The subject matter of the invention is a thickening agent based on at least one synthetic phyllosilicate which is characterized by the fact that it contains at least one additive from the following group of organic phosphorus compounds:

a) phosphonic acids with formula

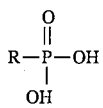

b) phosphinic acids with formula

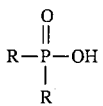

c) thiophosphinic acids with formula

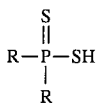

d) diesters of phosphorous acid with HO—P(OR)$_2$ e) diesters of phosphoric acid with formula

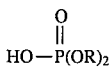

f) diphosphonic acids with formula

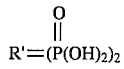

in which R is an alkyl or hydroxyalkyl group with 1 to 22 C atoms or an aryl or hydroxyaryl group with 6 to 12 C atoms and R' is an alkylene group with 2 to 22 C atoms.

DESCRIPTION OF THE INVENTION

Surprisingly it was found that by using the thickening agents according to the invention, the dispersion problems previously discussed can be solved. These novel products can be dispersed either as powders directly into the finished formulation without seeds or as pumpable pastes with the viscosity of these thickening agents in water reduced. In addition, highly concentrated pastes can be produced without the efficiency of the thickening agent in the system being impaired.

It is also possible by means of the thickening agents according to the invention to subsequently work powder into the finished systems without applying extreme shear forces.

The subject matter of the invention is also a process for producing a thickening agent according to the invention, addition being done either (a) as powder to the dry powder of the phyllosilicate; or (b) in dissolved form as a liquid at a suitable stage in the synthesis of the phyllosilicate, preferably to the filter cake.

The subject matter of the invention is also a master paste which is produced from the thickening agent according to the invention and which contains up to 35% by weight, preferably 5 to 25% by weight, especially 10 to 20% by weight solid.

The subject matter of the invention is also the use of the thickening agent according to the invention or master paste in liquid or flowable coating systems, i.e., which can be applied by coating, spraying, rolling etc., such as for example paints and varnishes, cosmetic and pharmaceutical preparations (such as creams and toothpastes), fertilizer suspensions, pesticide spray systems, undersealing compositions, bitumen emulsions, lubricating greases, polishing agents, printing inks, structural plasters, etc. With this product the rheology can be adjusted, in particular, its viscosity, stability (anti-settling effect, syneresis) and layer thickness (anti-sagging action).

The invention is detailed by the following examples.

EXAMPLES

Example 1

Three percent by weight of a synthetic hectorite was dispersed in 97% by weight demineralized water. For comparison, 3% by weight synthetic hectorite was dispersed in demineralized water with 1% by weight of additives listed below in Table I, relative to the amount of hectorite added (=0.03% of the total amount). The viscosity in the dispersion was measured in mPa.s (Viscolab LC 10, Physica).

The results are given in Table I.

TABLE I

| Thickening agent | Dosage | Additive | Dosage | Viscosity 1 h | 24 h |
|---|---|---|---|---|---|
| synthet. hectorite | 3% | 0 | 0 | 18500 | 26000 |
| synthet. hectorite | 3% | Na-polyphosphate | 1% | 16300 | 32000 |
| synthet. hectorite | 3% | Na-polyacrylate | 1% | 12000 | 20000 |
| synthet. hectorite | 3% | Hydroxyethane-1.1-di-phosphonic acid | 1% | 4200 | 9200 |

Example 2

A 3% gel of synthetic hectorite was produced in demineralized water analogously to Example 1. In comparison, gels with 3% by weight of the additives listed below (0.09% of total amount) were produced.

The viscosity of the gels is given in Table II.

TABLE II

| Thickening agent | Dosage | Additive | Dosage | Viscosity 1 h | 24 h |
|---|---|---|---|---|---|
| synthet. hectorite | 3% | 0 | 0 | 11700 | 19000 |
| synthet. hectorite | 3% | Na-polyphosphate | 3% | 9000 | 15000 |
| synthet. hectorite | 3% | Na-polyacrylate | 3% | 5800 | 10600 |
| synthet. hectorite | 3% | Hydroxyethane-1.1-di-phosphonic acid | 3% | 4 | 4 |
| synthet. hectorite | 3% | Na-phosphonate | 3% | 2760 | 6800 |

The results of Examples 1 and 2 show that the organic phosphorus compounds according to the invention reduce the viscosity of dispersions much more than conventional dispersion agents based on Na-polyphosphate or Na-acrylate. It is also recognizable that by increasing the amount added from 1% to 3% of the additive, the liquefying action is intensified.

Example 3

Synthetic hectorite from Example 1 was dispersed in demineralized water (dissolver, 5 minutes, 2800 rpm, from Pendraulik) and the viscosity of the gel obtained was measured in mPa.s after 1 h or 24 h in a Brookfield DV-II.

In comparison, the synthetic hectorite was mixed with the sodium salt of hydroxyethane-1,1-disphosphonic acid, homogenized and dispersed in demineralized water.

The results are listed in Table III.

TABLE III

| | % of synth. hectorite | % of additive | Dosage in water | Viscosity 1 h | 24 h |
|---|---|---|---|---|---|
| a) | 100% | 0% | 4% | 10600 | 19800 |
| b) | 100% | 0% | 6% | 56500 | 81700 |
| c) | 96% | 4% | 8% | 6 | 6 |
| d) | 94% | 6% | 25% | 1260 | 96 |

Example 4

Synthetic hectorite was mixed with phosphonic acid (Sapetin D100 from Woellner) or with Na-polyphosphate, homogenized, and dispersed in demineralized water analogously to Example 3. The viscosity was measured in a Viscolab LC 10 from Physica.

The results are listed in Table IV.

TABLE IV

| | % of synth. hectorite | % of additive | Dosage in water | Viscosity 1 h | 24 h |
|---|---|---|---|---|---|
| a) | 100% | 0% | 4% | 10600 | 19800 |
| b) | 100% | 0% | 6% | 56500 | 81700 |
| c) | 94% | 6% Phosphonic acid | 6% | 24600 | 42500 |
| d) | 94% | 6% Na-polyphosphate | 6% | 16800 | 28300 |
| e) | 94% | 6% Phosphonic acid | 4% | 6600 | 12600 |
| f) | 94% | 6% Na-polyphosphate | 4% | 2060 | 7080 |

Example 5

Analogously to Examples 3 and 4, the synthetic hectorite was homogeneously mixed with additives and a gel produced in tap water with the mixed product (stirred in the dissolver for 5 minutes at rpm) and the viscosity was measured (Viscolab LC 10)

The results are given in Table V.

TABLE V

| | % of synth. hectorite | % of additive | Dosage in water | Viscosity 1 h | 24 h |
|---|---|---|---|---|---|
| a) | 100% | 0% | 4% | 35800 | 77600 |
| b) | 100% | 0% | 6% | 85300 | 163700 |
| c) | 94% | 6% Phosphonic acid | 4% | 5420 | 7800 |
| d) | 94% | 6% Na-polyphosphate | 6% | 17100 | 25900 |

Examples 4 and 5 clearly show that the viscosity, mainly in tap water, can be reduced by adding standard dispersion agents. The liquefying action of the additive according to Example 3 however is not reached by far.

Example 6

As the viscosity of the master pastes, i.e., the thickening agents dispersed in water, is greatly reduced by the additives, it remains to be demonstrated that the thickening agent does in fact develop its effectiveness even in the finished system, as, for example, a paint.

This was tested with the following decorative paint (guideline formulation C-823 from ICI):

| Formulation: | Propylene glycol | 5.50 parts by weight |
|---|---|---|
| | Water | 7.75 parts by weight |
| | AMP-95 ® | 0.50 parts by weight |
| | Dehydran 1293 ® | 1.25 |
| | Surfynol 104 E ® | 1.00 |
| | Neocryl BT-24 ® | 7.25 |
| | $TiO_2$ (Tioxide TR-92) | 56.25 |

| Dispersion to <10 microns | | |
|---|---|---|
| Water | 8.50 | |
| Neocryl AH-24-C ® | 25.00 | 3 min, 930 rpm |
| Rheol. add. see Table VI | x | 10 min, 3720 rpm |
| Neocryl AH-24-C ® | 113.75 | 5 min, 930–2800 rpm |
| Diethylene glycol | 15.50 | 5 min, 930–1865 rpm |
| Dehydron 1293 ® | 2.25 | |
| Byk 154 ® | 1.75 | 5 min, 930–1865 rpm |

TABLE VI

| | Synth. hectorite | % of additive | Amount added in formulation | Viscosity mPa.s | Grain micron | Gloss 60°< | Sag at micron |
|---|---|---|---|---|---|---|---|
| a) | 100% | — | 0.9% | 144 | 100 | 54.3 | 150 |
| b) | 95% | 5% Na-polyphosphate | 0.9% | 188 | 50 | 50.5 | 150 |
| c) | 95% | 5% Phosphonic acid | 0.9% | 415 | 100 | 52.2 | 175 |
| d) | 95% | 5% Hydroxyethane-1-1-diphosphonic acid | 0.9% | 2841 | 40 | 62.2 | 300 |

Working-in took place as a powder. Primarily example (d) shows the outstanding effect of the thickening agent in the system.

Example 7

The action of the homogenized mixed products was also checked in a commercial, water-dilutable acrylic radiator paint. In this purchased paint (commercial product of Südwest Lacke & Farben) the thickening agent was worked in as a powder (in the dissolver, 15 minutes stirring, 2800 rpm).

Radiator paint undiluted: 1700 mPa.s
Gloss (60°<) : 79 5

| Synth. hectorite | % of additive | Amount added to paint | Viscosity | Gloss 60°< |
|---|---|---|---|---|
| 100% | — | 2% | 58,200 | 42.5 |
| 94% | 6% hydroxyethane diphosphonic acid-Na-salt | 2% | 98,400 | 57.8 |
| 94% | 6% Na-polyphosphate | 2% | 55,500 | 49.1 |
| 94% | 4% hydroxyethane diphosphonic acid-Na-salt | 2% | 89,600 | 55.2 |
| 98% | 2% hydroxyethane diphosphonic acid-Na-salt | 2% | 85,200 | 47.0 |

Example 8

The rheological additives according to the invention were also tested in a wood preservative stain in the following formulation.

| | Parts by Weight | |
|---|---|---|
| Water | 9.4 | |
| Rheol. add. see Table VIII | 20.0 | as 4% pre-gel in water |
| Lumiten in RBD ® | 0.4 | 10 min, dissolver, 930 rpm |
| Pigment distributor A ® | 0.4 | |
| Acronal A 627 ® | 136.0 | |
| Agitan 702 ® | 0.8 | |
| Propylene glycol | 10.0 | |
| Solvenon PP ® | 4.0 | 10 min, 930 rpm |
| Mergal S 96 ® | 6.0 | |
| Luconyl-water paste ® | 10.0 | 5 min, 930 rpm |

TABLE VIII

| Synth. hectorite | % of additive | Dosage in formulation | Viscosity mPa.s | Grain micron | Shine 60°< |
|---|---|---|---|---|---|
| 100% | — | 0.4% | 153 | 100 | 38.8 |
| 94% | 6% Na-polyphosphate | 0.4% | 175 | 90 | 60.6 |
| 94% | Hydroxyethane-1.1-diphosphonic acid | 0.4% | 148 | 15 | 75.7 |

Examples 6 through 8 clearly show that the rheological thickening agents which were modified from a synthetic phyllosilicate by adding an additive have an outstanding effect in coating systems. In spite of the "liquefaction" (viscosity reduction) of the parent paste, which is to some extent very dramatically pronounced, the action was preserved in the system or the action became even better in comparison to the unmodified version.

We claim:

1. A hydrophilic thickening agent based on at least one synthetic phyllosilicate, characterized in that it contains at least one additive selected from the group of organic phosphorous salts compounds comprising:

(a) phosphonic acids with formula

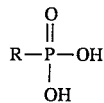

(b) phosphinic acids with formula

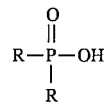

(c) thiophosphinic acids with formula

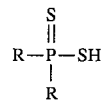

(d) diesters of phosphorous acid with formula
HO—P(OR)$_2$ (e) diesters of phosphoric acid with formula

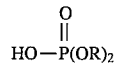

(f) diphosphonic acids with formula

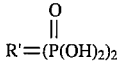

in which R is an alkyl or hydroxyalkyl group with 1 to 22 C atoms or an aryl or hydroxyaryl group with 6 to 12 C atoms and R' is an alkylene group with 2 to 22 C atoms.

2. The thickening agent of claim 1, wherein the proportion of the additive is between about 1 and about 20% by weight of the thickening agent.

3. The thickening agent of claim 1 wherein the proportion of the additive is between about 1% by weight and about 15% by weight of the thickening agent.

4. The thickening agent of claim 1 wherein the proportion of the additive is between about 2% by weight and about 10% by weight of the thickening agent.

5. The thickening agent of claim 1 wherein the proportion of the additive is between about 4% by weight and about 8% by weight of the thickening agent.

6. A process for producing the thickening agent of claim 1 comprising adding the additive as a powder to a dry powder of the phyllosilicate.

7. A process for producing the thickening agent of claim 1 comprising adding the additive in dissolved form as a liquid at a stage in the synthesis of the phyllosilicate.

8. The process of claim 7 wherein the additive is added to the phyllosilicate in the form of a filtered product.

9. A paste produced from the thickening agent of claim 1 wherein the paste contains from about 5 to about 35% by weight solid.

10. The paste of claim 9, wherein it contains the additive in an amount of from about 5% to about 20% by weight relative to the phyllosilicate.

11. A paste produced from the thickening agent of claim 1 wherein the paste contains about 5 to 25% by weight solid.

12. A paste produced from the thickening agent of claim 1 wherein the paste contains about 10 to 20% by weight solid.

13. A hydrophilic thickening agent based on at least one synthetic phyllosilicate, characterized in that it contains at least one additive present as an alkali salt selected from the group of organic phosphorous salts compounds comprising:

(a) phosphonic acids with formula

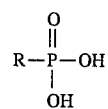

(b) phosphinic acids with formula

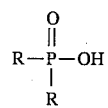

(c) thiophosphinic acids with formula

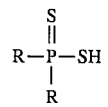

(d) diesters of phosphorous acid with formula
HO—P(OR)$_2$ (e) diesters of phosphoric acid with formula

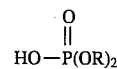

(f) diphosphonic acids with formula

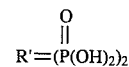

in which R is an alkyl or hydroxyalkyl group with 1 to 22 C atoms or an aryl or hydroxyaryl group with 6 to 12 C atoms and R' is an alkylene group with 2 to 22 C atoms.

14. The thickening agent of claim 13 wherein the alkali salt is a sodium salt.

* * * * *